(12) United States Patent
Parthasarathy et al.

(10) Patent No.: US 11,487,255 B1
(45) Date of Patent: Nov. 1, 2022

(54) INTEGRATED DETECTION SCHEME FOR FAST BLOOD FLOW MEASUREMENT

(71) Applicant: UNIVERSITY OF SOUTH FLORIDA, Tampa, FL (US)

(72) Inventors: Ashwin Bharadwaj Parthasarathy, Tampa, FL (US); Arindam Biswas, Tampa, FL (US); Arash Takshi, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 11 days.

(21) Appl. No.: 17/147,713

(22) Filed: Jan. 13, 2021

Related U.S. Application Data

(60) Provisional application No. 62/960,870, filed on Jan. 14, 2020.

(51) Int. Cl.
*G05B 15/02* (2006.01)
*G16H 40/67* (2018.01)
*A61B 5/026* (2006.01)
*H01L 31/02* (2006.01)
*G01N 21/47* (2006.01)
*A61B 5/02* (2006.01)

(52) U.S. Cl.
CPC ............ *G05B 15/02* (2013.01); *A61B 5/0261* (2013.01); *G01N 21/4738* (2013.01); *G16H 40/67* (2018.01); *H01L 31/02019* (2013.01); *A61B 5/02* (2013.01)

(58) Field of Classification Search
CPC ...... G05B 15/02; G16H 40/67; A61B 5/0261; A61B 5/02; G01N 21/4738; H01L 31/02019
See application file for complete search history.

(56) References Cited

U.S. PATENT DOCUMENTS

| 3,826,983 | A | * | 7/1974 | Garratt | .................. | G01R 17/06 |
| | | | | | | 324/99 D |
| 2009/0153865 | A1 | * | 6/2009 | Owa | .................. | G01N 21/274 |
| | | | | | | 356/440 |
| 2020/0396409 | A1 | * | 12/2020 | Posch | ................ | H04N 5/37455 |

OTHER PUBLICATIONS

Bi, R., et al. Deep tissue flowmetry based on diffuse speckle contrast analysis. Optics letters 38, 1401, (2013).
Dragojevic, T. et al. Compact, multi-exposure speckle contrast optical spectroscopy (SCOS) device for measuring deep tissue blood flow. Biomed Opt Express 9, 322-334, (2018).
Dragojevic, T. et al. High-speed multi-exposure laser speckle contrast imaging with a single-photon counting camera. Biomed Opt Express 6, 2865-2876, (2015).
Huang, C. et al. A Wearable Fiberless Optical Sensor for Continuous Monitoring of Cerebral Blood Flow in Mice. IEEE Journal of Selected Topics in Quantum Electronics 25, 1-8, (2019).

(Continued)

*Primary Examiner* — Jamil Ahmed
(74) *Attorney, Agent, or Firm* — Quarles & Brady LLP

(57) ABSTRACT

Disclosed are various embodiments for integrated diffuse correlation spectroscopy. A first control signal can be sent to a switch to cause an integrator to integrate a current from a photodiode. An integrated current can be received from the integrator, and a data signal can be sent to a computing device based at least in part on the integrated current. A second control signal can be sent to a switch to cause the integrator to cease integrating the current from the photodiode.

20 Claims, 7 Drawing Sheets

(56) References Cited

OTHER PUBLICATIONS

Huang, C. et al. Low-cost compact diffuse speckle contrast flowmeter using small laser diode and bare charge-coupled-device. Journal of Biomedical Optics 21, 080501-080501, (2016).
Huang, C. et al. Noncontact 3-D Speckle Contrast Diffuse Correlation Tomography of Tissue Blood Flow Distribution. IEEE Transactions on Medical Imaging 36, 2068-2076, (2017).
Liu, J., et al. Quantitative model of diffuse speckle contrast analysis for flow measurement. Journal of Biomedical Optics 22, 076016-076016, (2017).
Mazdeyasna, S. et al. Noncontact speckle contrast diffuse correlation tomography of blood flow distributions in tissues with arbitrary geometries. Journal of Biomedical Optics 23 (2018).
Valdes, C. P. et al. Speckle contrast optical spectroscopy, a non-invasive, diffuse optical method for measuring microvascular blood flow in tissue. Biomed Opt Express 5, 2769, (2014).

\* cited by examiner

INTEGRATED DETECTION SCHEME FOR FAST BLOOD FLOW MEASUREMENT

CROSS-REFERENCE TO RELATED APPLICATIONS

This application claims the benefit of and priority to U.S. Provisional Patent Application No. 62/960,870, entitled "INTEGRATED DETECTION SCHEME FOR FAST BLOOD FLOW MEASUREMENT," filed Jan. 14, 2020, the contents of which are incorporated by reference herein in their entirety.

BACKGROUND

Blood flow is an important indicator of tissue health since it directly informs the status of oxygen and nutrient supply to tissue. Thus, bedside monitoring of blood flow has significance in the treatment of a variety of diseases including strokes, traumatic brain injuries, cancers, and peripheral vascular disorders. The technique of Diffuse Correlation Spectroscopy (DCS) measures tissue blood flow from temporal intensity fluctuations of highly coherent light that has diffused through tissue. One primary limitation of conventional methods to estimate tissue dynamics with DCS is the need to use expensive, bulky, and high-sensitivity photon counting detectors and electronics that cannot be embedded directly into a low-cost probe.

BRIEF DESCRIPTION OF THE DRAWINGS

For a more complete understanding of the embodiments and the advantages thereof, reference is now made to the following description, in conjunction with the accompanying figures briefly described as follows.

DETAILED DESCRIPTION

Disclosed are various approaches for blood flow measurement using integrated diffuse correlation spectroscopy. The disclosed approaches are based on the measurement of blood flow using diffuse speckle contract (DCS) analysis. Traditional DCS relies on fast sampling of instantaneous intensity $i(t)$ fluctuations to estimate a blood flow index from the normalized autocorrelation of detected intensities. The disclosed approaches, on the other hand, include estimating tissue dynamics from the statistics of integrated photon intensities $I_t(T)$ sampled at measurement time t, where T is the time of integration. The integrated photon intensities can be given by:

$$I_t(T) = \frac{1}{T}\int_0^T i(t')dt' \quad (1)$$

The disclosed approaches accomplish measurement of $I_t(T)$ via direct integration of signals from a photodiode using low-power circuitry. The disclosed approaches allow detection of diffuse light fluctuations using a photodiode and an integrator circuit for simple, low-cost, board-level detection of speckle intensity fluctuations. The disclosed approaches facilitate fast, single-shot measurement of intensity dynamics over multiple integration times, with inherently reduced measurement noise, which is detected and compensated for in real-time.

In the following discussion, a general description of the system and its components is provided, followed by a discussion of the operation of the same.

Figure 1:
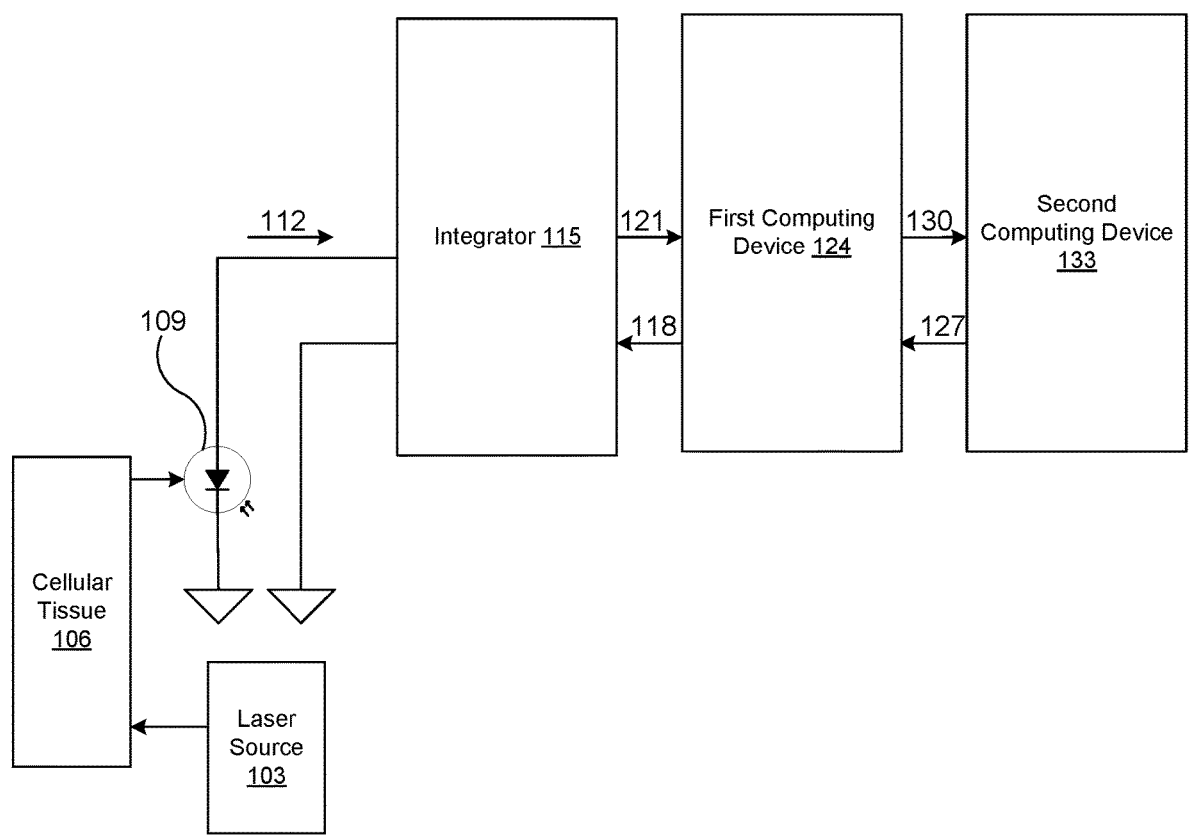
FIG. 1 is an example of a general arrangement for implementing integrated diffuse correlation spectroscopy according to various embodiments of the present disclosure.

Turning to FIG. 1, shown is an example of a general arrangement for implementing integrated diffuse correlation spectroscopy. A light source 103 can be used to illuminate tissue 106. The light source 103 will have a coherence length that is longer than the spread of light pathlengths in tissue as appropriate for the measurement geometry. The light source 103 can be any multi- or single-mode laser diode with associated collimation lenses/optics and/or temperature/wavelength stability circuits to satisfy the coherence condition. Photons from the light source 103 can diffuse through the tissue 106 and be received by a photodiode 109.

The photodiode 109 can be any suitable semiconductor device that outputs a photodiode current 112 upon receiving light. In some embodiments, a phototransistor or other photodetector can be used in place of or in addition to the photodiode 109. The photodiode 109 can be unbiased and operate in a photovoltaic mode such that the photodiode current 112 flows from an anode of the photodiode to a cathode of the photodiode.

The photodiode current 112 can be proportional to instantaneous speckle intensity fluctuations in the photons received by the photodiode 109. The photodiode 109 can also produce a dark current. The dark current can be a leakage current that flows through the photodiode 109 when no light hits the photodiode 109. In some embodiments, a pinhole (not shown) can be placed between the photodiode 109 and the tissue 106 to improve contrast of the photodiode 109.

The integrator 115 can receive the photodiode current 112 output by the photodiode 109 and integrate the photodiode current 112 to generate an integrated current 121. The integrator 115 can be any circuit or other device that can receive an input signal and generate an output signal that represents an integral of the input signal with respect to the time of integration. The integrator 115 can be implemented using an operational amplifier, a resistor-capacitor circuit, or other integrated circuit. The integrated current 121 can be given by:

$$V_0(T) \propto -\frac{1}{C_{int}} \int_0^T i_{in}(t)dt \qquad (2)$$

where T is the integration time, $C_{int}$ is the net capacitance in a feedback in the integrator 115, and $i_{in}(t) \propto I(t)$ is the instantaneous photodiode current 112.

The operation of the integrator 115 depends on one or more integration control signals 118 received by the integrator 115 from the first computing device 124. For example, the integrator 115 can receive an "ON" integration control signal 118 that causes the integrator 115 to integrate the photodiode current 112 and output an integrated current 121. As another example, the integrator 115 can receive a "reset" integration control signal 118 that causes the integrator 115 to reset and cease integrating the photodiode current 112.

The first computing device 124 can receive an input signal. The first computing device 124 can execute one or more read operations to read an input corresponding to the input signal. The first computing device 124 can record a photon intensity measurement for the input signal. The first computing device 124 can then output a data signal 130 comprising the photon intensity measurement for the input signal.

The input signal can be the integrated current 121, a dark current, or other input signal. For example, the first computing device 124 can receive the integrated current 121 from the integrator 115. The first computing device 124 can then read an input corresponding to the integrated current 121 and record a photon intensity measurement for the integrated current 121. In some embodiments, the first computing device 124 can correct for noise in the integrated current 121 caused by the dark current and record a corrected photon intensity measurement.

The first computing device 124 can act as a control mechanism for circuit control and data acquisition. The first computing device 124 can send one or more integration control signals 118 to the integrator 115 to control operation of the integrator. For example, the first computing device 124 can send an integration control signal 118 to the integrator 115 that causes the integrator 115 to begin integrating the photodiode current 112. As another example, the first computing device 124 can send an integration control signal 118 to the integrator 115 that causes the integrator 115 to reset and cease integrating the photodiode current 112.

The first computing device 124 can receive one or more commands 127 from the second computing device 133. The one or more commands 127 can trigger read operations on the first computing device 124. A first read operation can be executed at the same time as the integrator 115 begins integration. The first read operation can record the output of the integrator 115 at 'zero' integration time, thus measuring the dark current. Subsequent timed read operations record the integrated current at corresponding integration times. Multiple integration frames can be obtained by repeating this cycle. Measuring the dark current in the first read operation offers a method to correct for dark noise in each integration frame:

$$I_{corrected}(T) = I(T) - I_{dark} \qquad (3)$$

Speckle visibility or variance of intensity fluctuations at each integration time can be computed by estimating the standard deviation and mean intensities of the integration frames.

The second computing device 133 can send the commands 127 to the first computing device 124. These commands 127 can cause the first computing device 124 to send one or more integration control signals 118 to the integrator 115 to control operation of the integrator 115.

The second computing device 133 can receive the data signal 130 from the first computing device 124. The second computing device 133 can read data for the integration frames from the data signal 130 to compute speckle visibility and estimate blood flow using diffuse speckle contrast analysis. In some embodiments, functionality performed by the second computing device 133 can be performed by an application executable by the first computing device 124.

Figure 2:
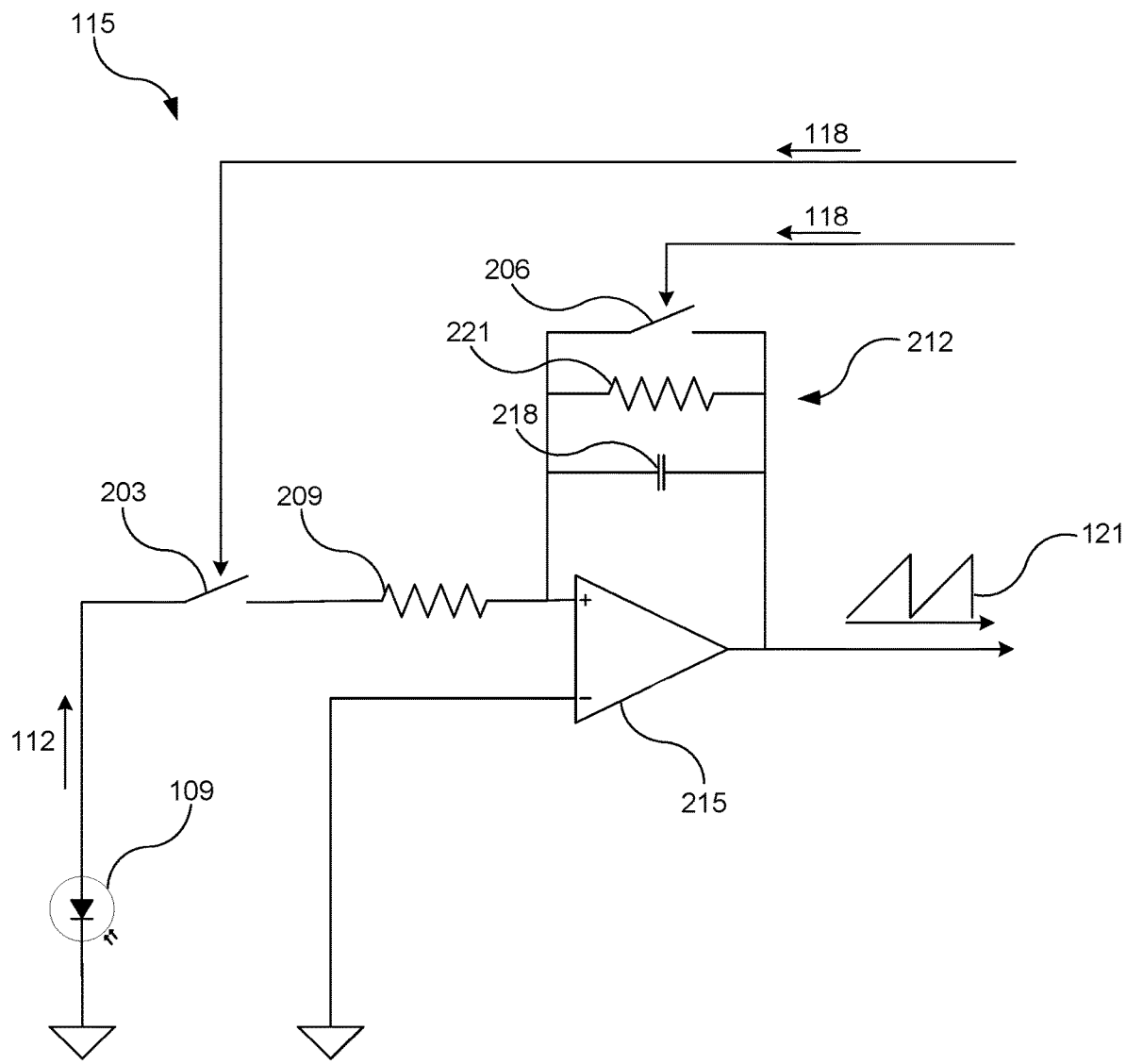
FIG. 2 is an example of one possible implementation of the integrator shown in FIG. 1 according to various embodiments of the present disclosure.

Turning to FIG. 2, shown is an example of a schematic of one possible implementation of the integrator 115. In this example, the integrator 115 is a circuit that includes an enable switch 203, a reset switch 206, a switch-amplifier resistor 209, a feedback loop 212, and an operational amplifier 215. FIG. 2 also shows the photodiode 109, which feeds the photodiode current 112 to the integrator 115.

The enable switch 203 and the reset switch 206 can be bipolar junction transistors, metal-oxide-semiconductor field-effect transistors (MOSFETs), or any other suitable switching devices. The enable switch 203 and the reset switch 206 can control the operation of the integrator 115. When the enable switch 203 is closed and the reset switch 206 is open, the integrator 115 can integrate the photodiode current 112 and output the integrated current 121. When the enable switch 203 is open and the reset switch 206 is closed, the integrator 115 will not integrate the photodiode current 112 and the integrator 115 can be reset. Each of the enable switch 203 and the reset switch 206 can open or close based on an integration control signal 118 received from the first computing device 124.

The switch-amplifier resistor 209 can be any suitable resistor or arrangement of resistors. The switch-amplifier resistor 209 can be connected between the enable switch 203 and the operational amplifier 215.

The feedback loop 212 can include a capacitor 218, a feedback resistor 221, and the reset switch 206. The capacitor 218 can be any suitable capacitor or arrangement of capacitors. For example, the capacitor 218 can be implemented as a single capacitor as shown in FIG. 2. As another example, the capacitor 218 can be implemented as a series or parallel configuration of more than one capacitor. The net capacitance of the feedback loop 212 can depend on the capacitance of the capacitor 218, and the net capacitance of the feedback loop 212 can determine the gain of the integrator 115. When the enable switch 203 is closed and the reset switch 206 is open, the capacitor 218 can accumulate charge while the integrator 115 integrates the photodiode current 112. When the enable switch 203 is open and the reset switch 206 is closed, the capacitor 218 can discharge through the operational amplifier 215 and the integrator 115 can be reset. The feedback resistor 221 can be any suitable resistor or arrangement of resistors. For example, the feedback resistor 221 can be implemented as a single resistor as shown in FIG. 2. As another example, the feedback resistor 221 can be implemented as a series or parallel configuration of more than one resistor.

The operational amplifier 215 can be any suitable operational amplifier comprising two input terminals and an output terminal. The operational amplifier 215 can receive the photodiode current 112 as an input via the switch-amplifier resistor 209. The operational amplifier can output the integrated current 121, which is likewise the output of the integrator 115.

Figure 3:
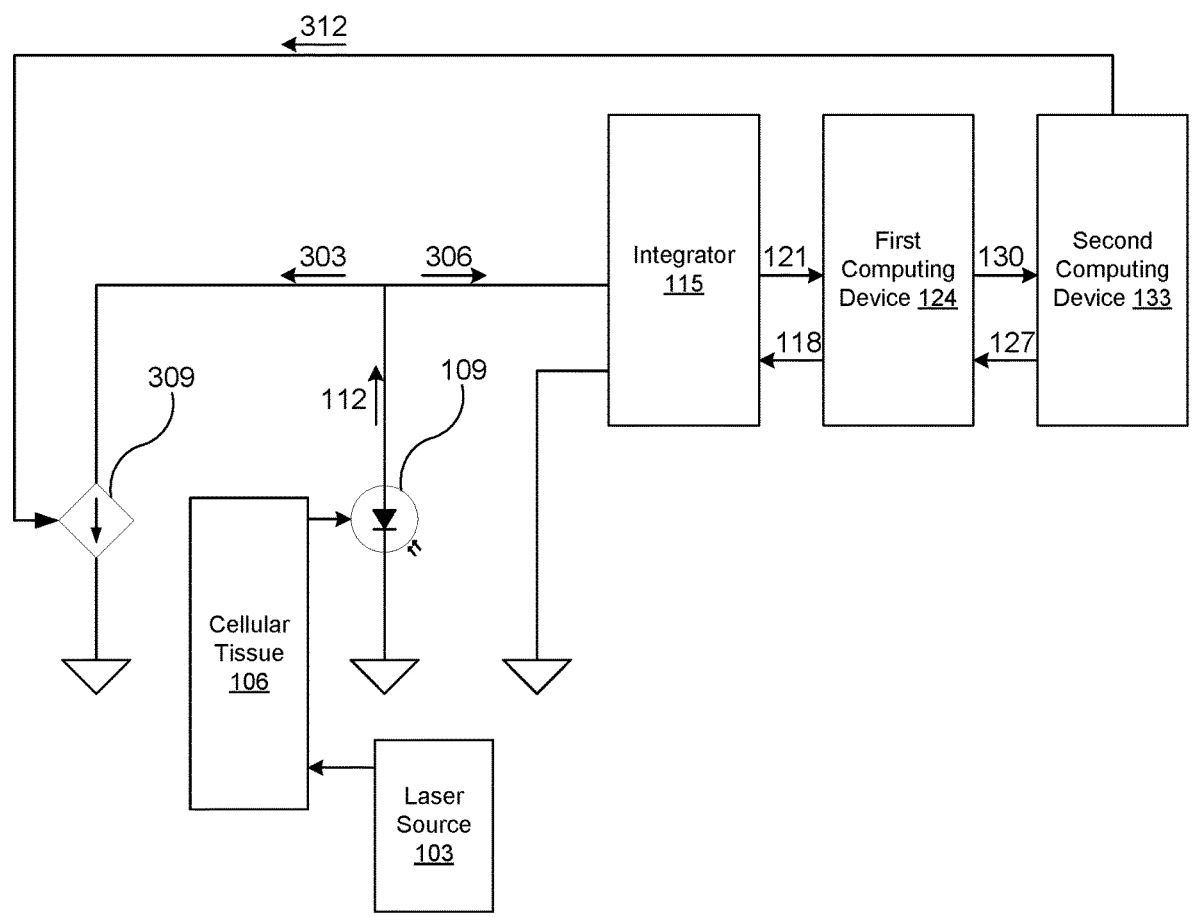
FIG. 3 is an example of a general arrangement for implementing integrated diffuse correlation spectroscopy with adaptive DC current subtraction according to various embodiments of the present disclosure.

Turning to FIG. 3, shown is an example of a general arrangement for implementing integrated diffuse correlation spectroscopy with adaptive DC current subtraction. In some examples, the photodiode 109 may have a detection area of the order of a few square millimeters, which is much larger than the average size of a single speckle. Thus, the photodiode current 112 represents a spatial average of several speckles, which can result in a non-fluctuating DC offset. Thus, the photodiode current 112 may in some cases have two components: a non-fluctuating DC current 303 generated by dark noise and speckle averaging, and a fluctuating signal current 306 generated by speckle intensity fluctuations. In effect, the photodiode current 112 can be modeled as:

$$I = I_{dc} + I_{sig}(t) \qquad (4)$$

where I is the photodiode current 112, $I_{dc}$ is the non-fluctuating DC current 303 that can represent a spatial averaging of multiple speckles, and $I_{sig}(t)$ is the fluctuating signal current 306 that can represent temporally varying speckle intensity fluctuations.

In some examples, the integrator 115 may integrate both the non-fluctuating DC current 303 and the fluctuating signal current 306. Blood flow information, however, may be contained in the fluctuating signal current 306. And the non-fluctuating DC current 303 component of the photodiode current 112 may be significantly larger than the fluctuating signal current 306 component, which can result in poor signal contrast and signal-to-noise ratio.

One approach to reduce the effects of the spatial averaging of speckles that results in the non-fluctuating DC current 303 is to use a photodiode 109 with a smaller active area or by using a pinhole a described in [0016]. But this may proportionally reduce the fluctuating signal current 306 and reduce the detection threshold of the photodiode 109. A better alternative is to actively suppress the non-fluctuating DC current 303. That way, the integrator 115 can integrate the fluctuating signal current 306.

The example of FIG. 3 shows an approach to subtract non-fluctuating DC current 303 generated by dark noise and speckle averaging from the from the photodiode current 112 by using a voltage-controlled current source 309. The voltage-controlled current source 309 can act as a drain/sink for the non-fluctuating DC current 303. For example, current drain through the voltage-controlled current source 309 can sink a programmable amount of the non-fluctuating DC current 303 from an input to the integrator 115, which can improve the signal contrast and signal-to-noise ratio in the integrated current 121.

The voltage-controlled current source 309 can be any suitable source of current whose intensity is controlled by a voltage elsewhere in the circuit. For example, the voltage-controlled current source can include an operational amplifier buffer and a MOSFET. As another example, the voltage-controlled current source can include a simple resistor and controlled voltage source. The amount of current through the voltage-controlled current source 309 can be controlled using a drain control signal 312. The drain control signal 312 can be received from the first computing device 124, second computing device 133 or any other suitable computing device.

Sinking the DC current in this way can result in a high signal-to-noise ratio of the integrated speckle intensity fluctuations. The magnitude of the integrated current 121 output can be decreased since the non-fluctuating DC current 303 is removed from the photodiode current 112. The variance of the integrated current 121, however, can be significantly increased.

Figure 4:
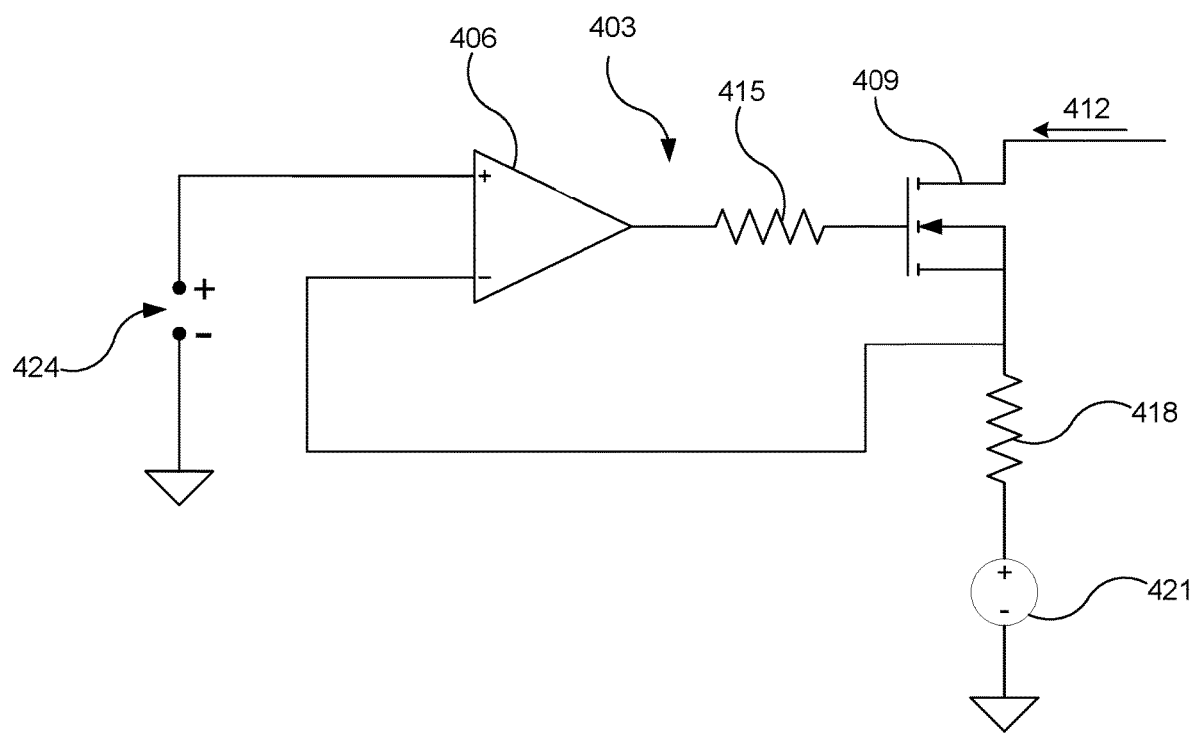
FIG. 4 is an example of schematic of one possible implementation of the voltage-controlled current source shown in FIG. 3 according to various embodiments of the present disclosure.

Turning to FIG. 4, shown is an example of schematic of one possible implementation of the voltage-controlled current source 309. A current drain path 403 can be implemented that includes an operational amplifier buffer 406 that drives a MOSFET 409 controlling an amount of a drain current 412. The voltage-controlled current source can further include a buffer-MOSFET resistor 415, a MOSFET-source resistor 418, and a DC voltage source 421.

The operational amplifier buffer 406 can be any suitable operational amplifier comprising two input terminals and an output terminal. Input to the operational amplifier buffer 406 can be an input voltage 424 that can be controlled by the drain control signal 312 from the first computing device 124.

The MOSFET 409 can be an n-channel enhancement mode MOSFET. In some examples, however, other varieties of MOSFET or other electrical components suitable for controlling an amount of a current may also be used. The buffer-MOSFET resistor 415 and the MOSFET-source resistor 418 can each be any suitable resistor or arrangement of resistors. The buffer-MOSFET resistor 415 can be connected between the operational amplifier buffer 406 and a gate terminal of the MOSFET 409. The MOSFET-source resistor 418 can be connected between a source terminal of the MOSFET 409 and the DC voltage source 421. The DC voltage source 421 can be any suitable source of DC voltage.

The drain current 412 can be a function of an input voltage 424 to the operational amplifier buffer 406. In some examples, the input voltage 424 to the operational amplifier buffer 406 can be controlled by the first computing device 124, the second computing device 133, or other computing device. The signal contrast and signal-to-noise ratio can be at a maximum when the input voltage 424 is controlled in a manner that causes the drain current 412 to become equal to the non-fluctuating DC current 303.

Figure 5:
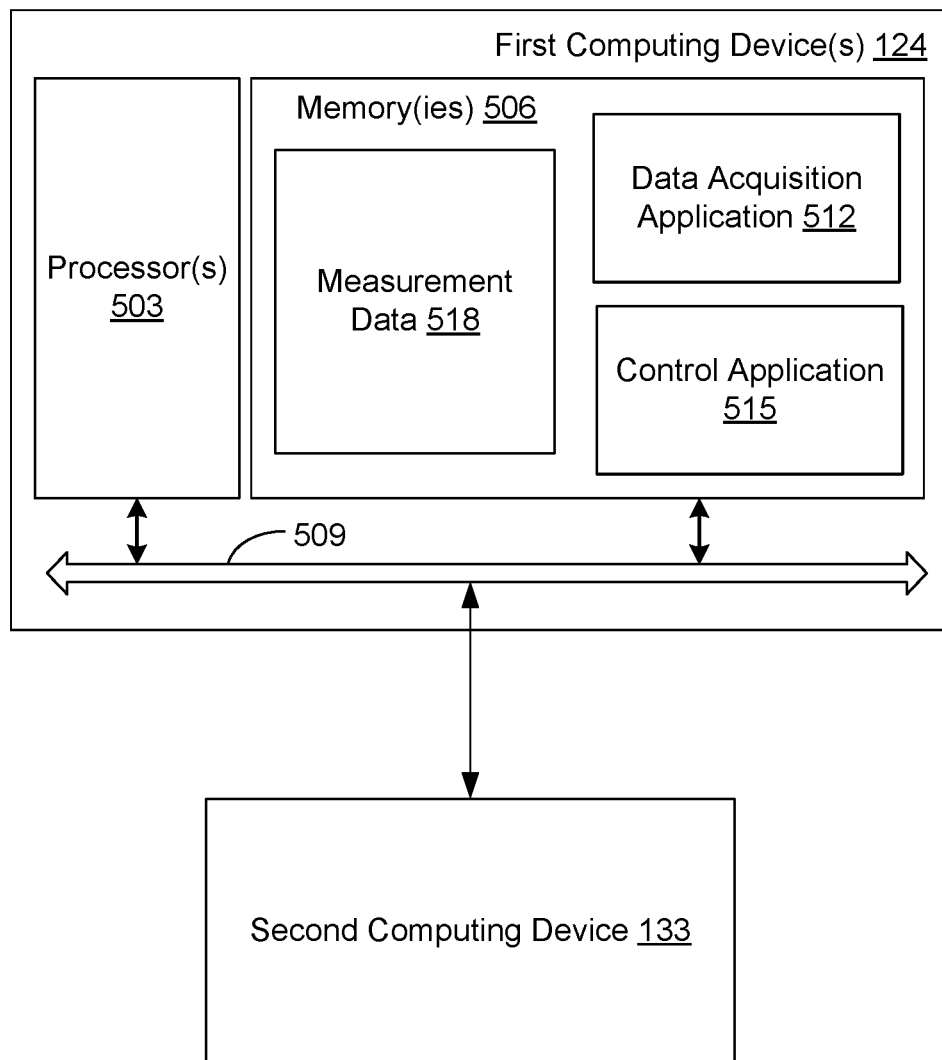
FIG. 5 is an example of a schematic block diagram of the first computing device and the second computing device shown in FIGS. 1 and 3 according to various embodiments of the present disclosure.

Turning to FIG. 5, shown are one or more first computing devices 124 in data communication with a second computing device 133. Each first computing device 124 includes a processor 503 and a memory 506, each of which is electrically and communicatively coupled to a local interface 509. To this end, each first computing device 124 may represent a server computer, a client computing device (e.g., personal computer, mobile device, smartphone, tablet, wearable computing device, etc.), a single-board computer (e.g., a microcontroller, system-on-a-chip (SoC), or similar device). The local interface 509 may include a data bus with an accompanying address/control bus or other bus structure.

Stored in the memory 506 are both data and several components that are executable by the processor 503. In particular, stored in the memory 506 and executable by the processor 503 are a data acquisition application 512, a control application 515, and potentially other applications. Also stored in the memory 506 may be measurement data 518 and other data. In addition, an operating system may be stored in the memory 506 and executable by the processor 503.

It is understood that there may be other applications that are stored in the memory 506 and are executable by the processor 503. Where any component discussed herein is implemented in the form of software, any one of a number of programming languages may be employed such as, for example, C, C++, C#, Objective C, Java®, JavaScript®, Perl, PHP, Visual Basic®, Python®, Ruby, or Flash®.

A number of software components are stored in the memory 506 and are executable by the processor 503. In this respect, the term "executable" means a program file that is in a form that can ultimately be run by the processor 503. Examples of executable programs may be, for example, a compiled program that can be translated into machine code in a format that can be loaded into a random access portion of the memory 506 and run by the processor 503, source code that may be expressed in proper format such as object code that is capable of being loaded into a random access portion of the memory 506 and executed by the processor 503, or source code that may be interpreted by another executable program to generate instructions in a random access portion of the memory 506 to be executed by the processor 503, etc. An executable program may be stored in any portion or component of the memory 506 including, for example, random access memory (RAM), read-only memory (ROM), hard drive, solid-state drive, Universal Serial Bus (USB) flash drive, memory card, optical disc such as compact disc (CD) or digital versatile disc (DVD), floppy disk, magnetic tape, or other memory components.

The processor 503 may represent multiple processors 503 or multiple processor cores and the memory 506 may represent multiple memories 506 that operate in parallel processing circuits, respectively. In such a case, the local interface 509 may be an appropriate network that facilitates communication between any two of the multiple processors 503, between any processor 503 and any of the memories 506, or between any two of the memories 506. The local interface 509 may include additional systems designed to coordinate this communication, including, for example, performing load balancing. The processor 503 may be of electrical or of some other available construction.

The memory 506 is defined herein as including both volatile and nonvolatile memory and data storage components. Volatile components are those that do not retain data values upon loss of power. Nonvolatile components are those that retain data upon a loss of power. Thus, the memory 506 may include, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, or other memory components, or a combination of any two or more of these memory components. In addition, the RAM may include, for example, static random-access memory (SRAM), dynamic random access memory (DRAM), or magnetic random access memory (MRAM) and other such devices. The ROM may include, for example, a programmable read-only memory (PROM), an erasable programmable read-only memory (EPROM), an electrically erasable programmable read-only memory (EEPROM), or other like memory device.

The data acquisition application 512 represents an application that reads an input corresponding to an input signal received from the integrator 115. The data acquisition application 512 can execute one or more read operations to read the input signal. This input signal can be, for example, the integrated current 121 or a dark current. The data acquisition application can record a photon intensity measurement for the input signal in the measurement data 518. The data acquisition application can send a data signal 130 comprising at least a portion of the measurement data 518 to the second computing device 133.

The control application 515 represents an application that controls operation of the integrator 115 by sending one or more integration control signals 118 to the integrator 115. For example, the control application 515 can generate integration control signals 118 to turn 'ON' integration operation or 'reset' the integrator 115. This way, the control application 515 can control the timing of integration by generating integration control signals 118 to control integration and reset of the integrator 115. The control application 515 can send the integration control signals 118 based on commands received from the second computing device 133. In some examples, the control application 515 can control operation of the voltage-controlled current source 309 by sending one or more drain control signals 312 to the voltage-controlled current source 309. For example, the control application 515 can generate a drain control signal 312 to set an input voltage 424 of the voltage-controlled current source 309.

The measurement data 518 represents recorded measurements of integrated photon intensities for input signals received by the first computing device 124 at various integration times. For each read operation executed by the data acquisition application 512, the data acquisition application 512 can record a photon intensity measurement for the input signal in the measurement data 518. A data signal 130 comprising at least a portion of the measurement data 518 can be sent to the second computing device 133.

The second computing device 133 can comprise any system providing computing capability. The second computing device 133 can receive a data signal 130 comprising at least a portion of the measurement data 518. The second computing device 133 can read the integration frames from the data signal 130 to compute speckle visibility and estimate blood flow using diffuse speckle contrast analysis. The second computing device 133 can send one or more commands 127 to the control application 515. These commands 127 can instruct the control application 515 to send one or more integration control signals 118 to the integrator 115. The integration control signals 118 can control the integration and reset of the integrator 115. The command 127 can also specify how many photon intensity measurements are to be obtained before the integrator 115 is reset.

In some examples, a command 127 can instruct the control application 515 to send one or more drain control signals 312 to the voltage-controlled current source 309. The drain control signals 312 can control an input voltage 424 of the voltage-controlled current source 309. The command 127 can also specify an input voltage 424 of the voltage-controlled current source 309. In some examples, however, functionality performed by the second computing device 133 can be performed by an application executable by the first computing device 124.

Figure 6:
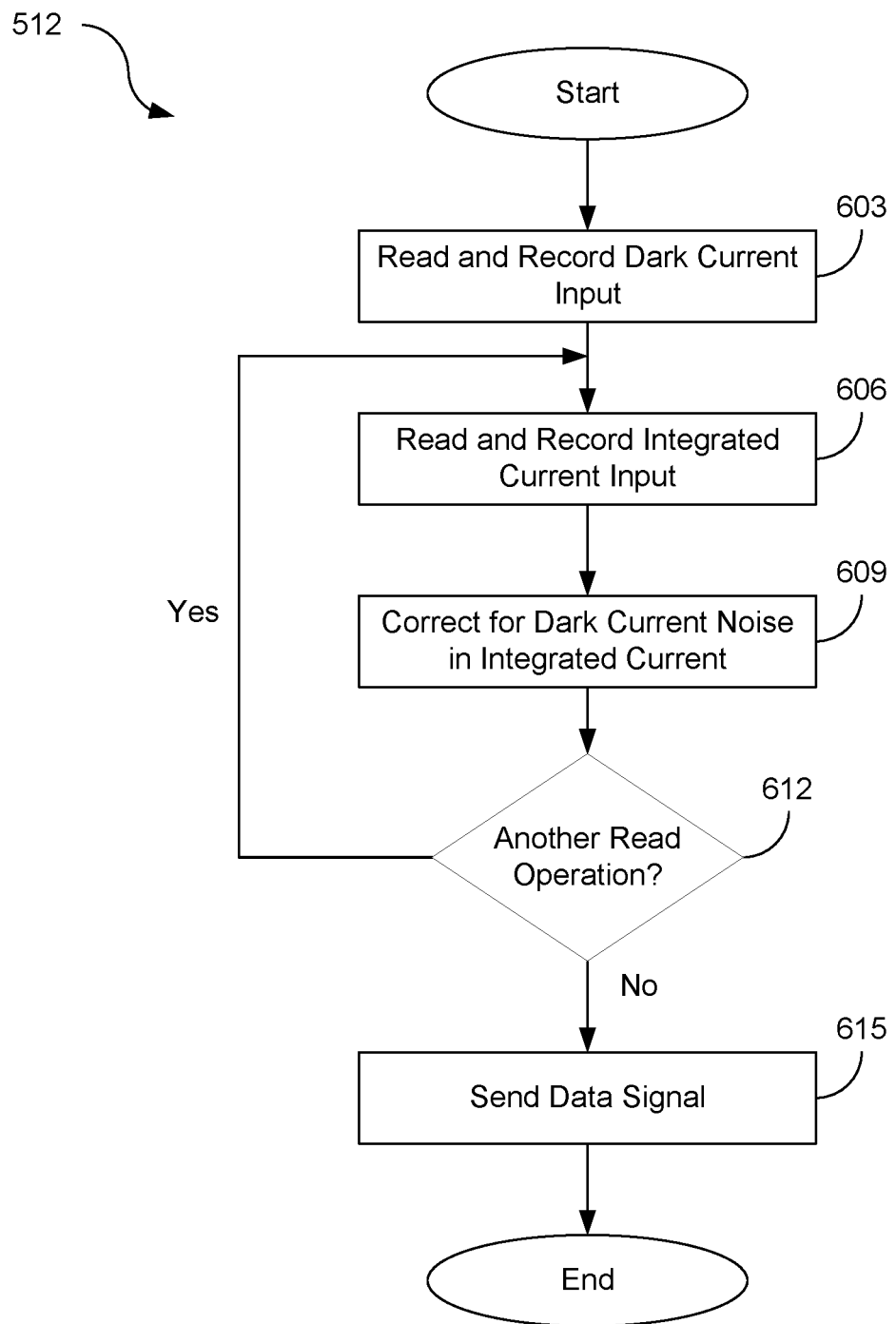
FIG. 6 is an example flowchart of certain functionality implemented by portions of a data acquisition application executed by the first computing device shown in FIGS. 1 and 3 according to various embodiments of the present disclosure.

Turning to FIG. 6, shown is a flowchart that provides one example of the operation of a portion of the data acquisition application 512 according to various embodiments. It is understood that the flowchart of FIG. 6 provides merely an example of the many different types of functional arrangements that may be employed to implement various embodiments of the present disclosure. As an alternative, the flowchart of FIG. 6 may be viewed as depicting an example of elements of a method implemented according to one or more embodiments.

Beginning with box 603, the data acquisition application 512 executes a read operation to record an input corresponding to a dark current received at the first computing device 124. This read operation can be executed when the control application 315 sends an integration control signal 118 that causes the integrator 115 to begin integration. This can allow the dark current to be measured before the integrated current 121 is received at the first computing device 124. The dark current can be any leakage current flowing from the photodiode 109 that is generated irrespective of photons received by the photodiode 109.

Then, at box 606, the data acquisition application 512 executes a read operation to record an input corresponding to an integrated current 121 received at the first computing device 124. This read operation can be executed after the control application 315 sends an integration control signal 118 that causes the integrator 115 to begin integration. A photon intensity measurement for the integrated current 121 can be recorded in the measurement data 318.

Proceeding to box 609, the data acquisition application 512 corrects for dark current noise in the integrated current 121 recorded at box 606. For example, the photon intensity measurement for the dark current recorded at box 603 can be subtracted from the photon intensity measurement for the integrated current 121. A corrected photon intensity measurement can then be recorded in the measurement data 318.

Proceeding then to box 612, the data acquisition application 512 determines whether to execute another read operation. Whether the data acquisition application 512 executes another read operation can depend on how many photon intensity measurements are to be recorded for a given integration frame. The data acquisition application 512 can execute subsequent read operations to obtain multiple photon intensity measurement for a given integration frame. If another read operation is to be executed, execution of the data acquisition application 512 proceeds back to box 606. If another read operation is not to be executed, execution of the data acquisition application 512 proceeds to box 615.

At box 615, the data acquisition application 512 sends a data signal 130 to the second computing device 133. The data signal 130 can be based on the measurement data 318. For example, the data signal 130 can include data on fluctuations in the photon intensities measured during integration.

Figure 7:
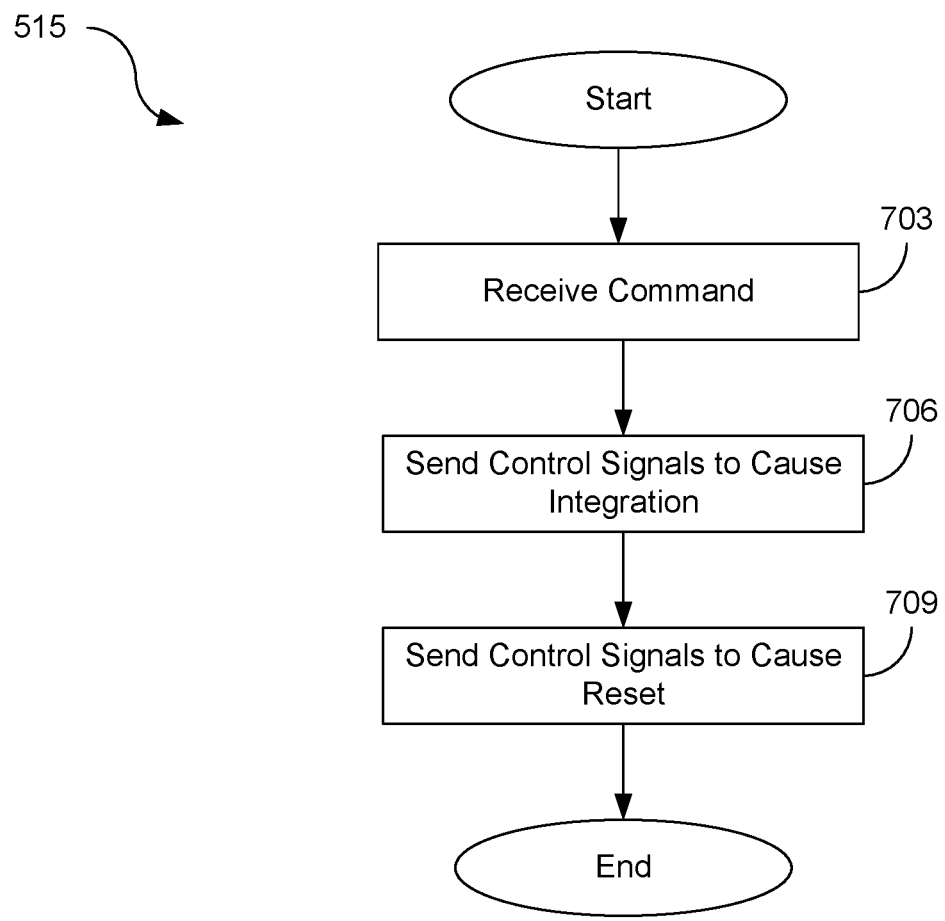
FIG. 7 is an example flowchart of certain functionality implemented by portions of a control application executed by the first computing device shown in FIGS. 1 and 3 according to various embodiments of the present disclosure.

Turning to FIG. 7, shown is a flowchart that provides one example of the operation of a portion of the control application 515 according to various embodiments. It is understood that the flowchart of FIG. 7 provides merely an example of the many different types of functional arrangements that may be employed to implement various embodiments of the present disclosure. As an alternative, the flowchart of FIG. 7 may be viewed as depicting an example of elements of a method implemented according to one or more embodiments.

Beginning with box 703, the control application 515 receives a command 127 from the second computing device. The command 127 instructs the control application to cause the integrator 115 to begin integrating the photodiode current 112. The command 127 can also include instructions on how many photon intensity measurements are to be recorded by the data acquisition application 512 before the control application 515 causes the integrator 115 to cease integrating the photodiode current 112 and reset.

Next, at box 706, the control application 515 sends at least one first integration control signal 118 to the integrator 115. The first integration control signal 118 can cause the integrator 115 to begin integration. For example, the first integration control signal 118 can cause a number of switches in the integrator 115 to open or close such that the integrator 115 begins integrating the photodiode current 112. The control signal may also be used to operate the voltage-controlled current source 309.

Proceeding to box 709, the control application 515 sends at least one second integration control signal 118 to the integrator 115. The second integration control signal 118 can cause the integrator to reset and cease integrating the photodiode current 112. The control application 515 can send the second integration control signal 118 once a number of photon intensity measurements are obtained by the data acquisition application 512.

Although the data acquisition application 512, the control application 515, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts of FIGS. 4 and 5 show the functionality and operation of an implementation of portions of the data acquisition application 512 or the control application 515. If embodied in software, each block may represent a module, segment, or portion of code that includes program instructions to implement the specified logical function(s). The program instructions may be embodied in the form of source code that includes human-readable statements written in a programming language or machine code that includes numerical instructions recognizable by a suitable execution system such as a processor 503 in a computer system or other system. The machine code may be converted from the source code through various processes. For example, the machine code may be generated from the source code with a compiler prior to execution of the corresponding application. As another example, the machine code may be generated from the source code concurrently with execution with an interpreter. Other approaches can also be used. If embodied in hardware, each block may represent a circuit or a number of interconnected circuits to implement the specified logical function or functions.

Although the flowcharts of FIGS. 4 and 5 show a specific order of execution, it is understood that the order of execution may differ from that which is depicted. For example, the order of execution of two or more blocks may be scrambled relative to the order shown. Also, two or more blocks shown in succession in FIGS. 4 and 5 may be executed concurrently or with partial concurrence. Further, in some embodiments, one or more of the blocks shown in FIGS. 4 and 5 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the data acquisition application 512 and the control application 515, that includes software or code can be embodied in any non-transitory computer-readable medium for use by or in connection with an instruction execution system such as, for example, a processor 503 in a computer system or other system. In this sense, the logic may include, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can include any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the data acquisition application 512 and the control application 515, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device, or in multiple computing devices in the same computing environment or computing cluster.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X; Y; Z; X and/or Y; X and/or Z; Y and/or Z; X, Y, and/or Z, etc). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiments without departing substantially from the spirit and principles of the disclosure. All such modifications and variations are intended to be included herein within the scope of this disclosure and protected by the following claims.

Therefore, at least the following is claimed:

1. A system comprising:
    a photodiode configured to output a photodiode current based at least in part on a plurality of photons received by the photodiode;
    an integration circuit configured to output an integrated current based at least in part on the photodiode current;
    a first computing device comprising a processor and a memory; and
    machine-readable instructions stored in the memory that, when executed by the processor, cause the first computing device to at least:
        send a first control signal to a switch in response to receiving a first command from a second computing device, the first control signal causing the integration circuit to begin outputting the integrated current;
        receive an integrated current from an integration circuit;
        read an input corresponding to the integrated current; and
        send a second control signal to the switch in response to receiving a second command from the second computing device, the second control signal causing the integration circuit to cease outputting the integrated current.

2. The system of claim 1, wherein the machine-readable instructions, when executed by the processor, further cause the first computing device to at least send a data signal to the second computing device, the data signal being based at least in part on the integrated current.

3. The system of claim 1, further comprising a voltage-controlled current source, wherein the machine-readable instructions, when executed by the processor, further cause the first computing device to at least send a drain control signal to the voltage-controlled current source, the drain control signal specifying a value of an input voltage for the voltage-controlled current source.

4. The system of claim 3, wherein the voltage-controlled current source comprises an operational amplifier and a metal-oxide-semiconductor field effect transistor.

5. The system of claim 1, wherein the integrated current is a function of a time of integration.

6. The system of claim 1, wherein the plurality of photons is diffused through tissue.

7. The system of claim 1, wherein the photodiode current is proportional to speckle intensity fluctuations of the plurality of photons.

8. The system of claim 1, wherein the photodiode operates in a photovoltaic mode such that a photodiode current flows from an anode of the photodiode to a cathode of the photodiode.

9. The system of claim 1, wherein the integration circuit comprises an operational amplifier.

10. The system of claim 1, wherein the integration circuit comprises a resistor-capacitor circuit.

11. A method, comprising:
    sending, by a first computing device, an activate integration control signal to a switch in response to receiving a first command from a second computing device;
    receiving, by the first computing device, an integrated current from an integration circuit, the integrated current being based at least in part on a photodiode current generated by a photodiode;
    reading, by the first computing device, an input corresponding to the integrated current; and
    sending, by the first computing device, a reset integration control signal to the switch in response to receiving a second command from the second computing device.

12. The method of claim 11, wherein sending the activate integration control signal to the switch further comprises:
    sending, by the first computing device, a first activate integration control signal to a first switch, wherein the first activate integration control signal causes the first switch to close; and
    sending, by the first computing device, a second activate integration control signal to a second switch, wherein the second activate integration control signal causes the second switch to open.

13. The method of claim 11, wherein sending the activate integration control signal to the switch causes the integration circuit to integrate a signal from a photodiode.

14. The method of claim 11, wherein sending the reset integration control signal to the switch comprises:

sending, by the first computing device, a first integration reset control signal to a first switch, wherein the first integration reset control signal causes the first switch to open; and sending, by the first computing device, a second integration reset control signal to a second switch, wherein the second integration reset control signal causes the second switch to close.

15. The method of claim 11, further comprising sending, by the first computing device, a drain control signal to a voltage-controlled current source.

16. The method of claim 15, wherein the drain control signal causes the voltage-controlled current source to generate an input voltage.

17. A non-transitory, computer-readable medium embodying an application executable in at least one computing device, that, when executed, causes the at least one computing device to at least:

send a drain control signal to a voltage-controlled current source in response to receiving a first command from another computing device, the drain control signal causing the voltage-controlled current source to generate an input voltage;

send a first integration control signal to a switch in response to receiving a second command from the other computing device, the first integration control signal causing the switch to close;

read an input corresponding to an integrated current; and send a second integration control signal to the switch in response to receiving a third command from the other computing device, the second integration control signal causing the switch to open.

18. The non-transitory computer-readable medium of claim 17, wherein application, when executed, further causes the at least one computing device to at least:

receive a dark current, wherein the dark current comprises a leakage current that flows through a photodiode; and read an input corresponding to the dark current.

19. The non-transitory computer-readable medium of claim 18, wherein the application, when executed, further causes the at least one computing device to at least determine a corrected current based at least in part on the integrated current and the dark current.

20. The non-transitory computer-readable medium of claim 17, wherein:

the first command comprises a number of volts;

the second command comprises instructions to cause an integration circuit to begin integration; and the third command comprises instructions to cause the integration circuit to cease integration.

* * * * *